(12) United States Patent
Tameze

(10) Patent No.: US 9,464,086 B2
(45) Date of Patent: Oct. 11, 2016

(54) CRYSTALLINE FORMS OF N,N-DICYCLOPROPYL-4-(1,5-DIMETHYL-1 H-PYRAZOL-3-YLAMINO)-6-ETHYL-1-METHYL-1,6-DIHYDROIMIDAZO[4,5-D] PYRROLO[2,3-B]PYRIDINE-7-CARBOXAMIDE FOR THE TREATMENT OF MYELOPROLIFERATIVE DISORDERS

(71) Applicant: BRISTOL-MYERS SQUIBB COMPANY, Princeton, NJ (US)

(72) Inventor: Shella Tameze, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/892,637

(22) PCT Filed: May 28, 2014

(86) PCT No.: PCT/US2014/039657
§ 371 (c)(1),
(2) Date: Nov. 20, 2015

(87) PCT Pub. No.: WO2014/193881
PCT Pub. Date: Dec. 4, 2014

(65) Prior Publication Data
US 2016/0130272 A1    May 12, 2016

Related U.S. Application Data

(60) Provisional application No. 61/828,760, filed on May 30, 2013.

(51) Int. Cl.
*C07D 221/22* (2006.01)
*C07D 471/14* (2006.01)

(52) U.S. Cl.
CPC .................. *C07D 471/14* (2013.01)

(58) Field of Classification Search
CPC ..................................... C07D 401/06
USPC .......................................... 546/79
See application file for complete search history.

(56) References Cited

U.S. PATENT DOCUMENTS

| 8,202,881 B2 | 6/2012 | Purandare et al. |
| 8,673,933 B2 | 3/2014 | Purandare et al. |
| 2011/0059943 A1 | 3/2011 | Purandare et al. |
| 2013/0225551 A1 | 8/2013 | Purandare et al. |

FOREIGN PATENT DOCUMENTS

| WO | WO 2011/028864 A1 | 3/2011 |
| WO | WO2014/193865 A1 | 5/2014 |
| WO | WO2014/193866 A1 | 5/2014 |
| WO | WO2014/193887 A1 | 5/2014 |

OTHER PUBLICATIONS

Caira M.R, Crystalline Polymorphism of Organic Compounds, Topics in Current Chemistry, Jan. 1, 1998, vol. 198, pp. 163-208.

*Primary Examiner* — Nizal Chandrakumar
(74) *Attorney, Agent, or Firm* — Elliott Korsen

(57) ABSTRACT

Crystalline form, Form N-2, of N,Ndicyclopropyl-4-(1,5-dimethyl-1Hpyrazol-3-ylamino)-6-ethyl-1-methyl-1,6-dihydroimidazo[4,5-d]pyrrolo[2,3-b]pyridine-7-carboxamide (Compound I) is provided. Also provided are a pharmaceutical composition and an oral dosage form comprising Form N-2 of Compound I as well as a method of using the Form N-2 of Compound I in the treatment of myeloproliferative disorders, which include polycythaemia vera, thrombocythaemia and primary myelofibrosis.

2 Claims, 3 Drawing Sheets

CRYSTALLINE FORMS OF N,N-DICYCLOPROPYL-4-(1,5-DIMETHYL-1H-PYRAZOL-3-YLAMINO)-6-ETHYL-1-METHYL-1,6-DIHYDROIMIDAZO[4,5-D]PYRROLO[2,3-B]PYRIDINE-7-CARBOXAMIDE FOR THE TREATMENT OF MYELOPROLIFERATIVE DISORDERS

CROSS REFERENCE TO RELATED APPLICATIONS

This application claims priority from U.S. Provisional Application No. 61/828,760 filed May 30, 2013, the disclosure of which is incorporated herein by reference in its entirety.

FIELD OF THE INVENTION

The present invention generally relates to a crystalline form of N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide, a JAK2 inhibitor currently in clinical trials for the treatment of myeloproliferative disorders, which include polycythaemia vera, thrombocythaemia and primary myelofibrosis.

BACKGROUND OF THE INVENTION

N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide, has the structure of formula I:

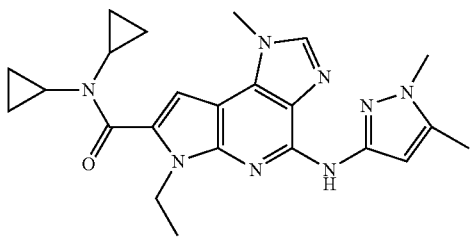

(I)

Compound I, compositions comprising Compound I, and methods of using Compound I are disclosed in U.S. Pat. No. 8,202,881 B2, which is assigned to the present assignee and is incorporated herein by reference in its entirety.

Typically, in the preparation of a pharmaceutical composition, a form of the active ingredient is sought which has the desired solubility and bioavailability and has sufficient stability that it does not convert during manufacture or storage of the pharmaceutical composition to a different form having different solubility and/or bioavailability. A form of Compound I is desired having properties and stability that allow the preparation of pharmaceutical compositions suitable for the treatment of diseases such as cancer. It has been found through extensive investigation that the form disclosed in this application is the most desirable identified to date with regard to chemical/physical stability, reproducibility and hygroscopicity.

SUMMARY OF THE INVENTION

In one embodiment, the compound of Example 1

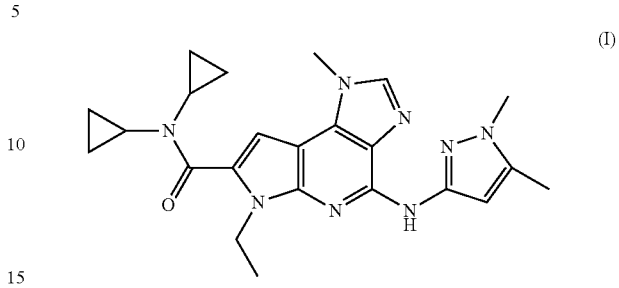

(I)

is provided as a crystalline material comprising the first crystalline form. The first crystalline form of the compound of Example 1 comprises a neat crystalline form referred to herein as "Form N-2" or "N-2 Form" of Example 1.

In one embodiment, the N-2 Form of Example 1 is characterized by unit cell parameters approximately equal to the following:

Cell Dimensions:
  a=13.4233(2) Å
  b=10.4312(2) Å
  c=16.3355(2) Å
  α=90°
  β=90.4750(10)°
  γ=90°
Volume=2287.24(6) Å$^3$
Crystal system: Monoclinic
Space group: P2$_1$/n
Molecules/asymmetric unit: 1
Number of molecules in the unit cell=4
Density (calculated)=1.256 Mg/m$^3$
Measurement of the crystalline form is at a temperature of about 23° C.

In another embodiment, the N-2 Form is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, Form N-2 may be characterized by a powder X-ray diffraction pattern comprising the following 2θ values (CuKα λ=1.5418 Å): 8.5±0.2, 10.0±0.2, 10.8±0.2, 13.2±0.2, 13.7±0.2, 15.2±0.2, 16.6±0.2, 18.2±0.2, 19.1±0.2, 20.5±0.2, 22.2±0.2 and 24.1±0.2, at room temperature.

In still yet an even further embodiment, the N-2 Form is substantially pure.

In still yet another embodiment, the N-2 Form contains at least about 90 wt. %, preferably at least about 95 wt. %, and more preferably at least about 99 wt. %, based on weight of the Form N-2.

In yet another embodiment, a substantially pure, N-2 Form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline Form N-2 has substantially pure phase homogeneity with less than about 1% of the total peak area of the experimentally measured PXRD pattern arising from peaks that are absent from the simulated PXRD pattern.

In another embodiment, the crystalline form consists essentially of Form N-2. The crystalline form of this embodiment may comprise at least about 90 wt. %, preferably at least about 95 wt. %, and more preferably at least about 99 wt. %, based on the weight of the crystalline form, Form N-2.

In yet another embodiment, a pharmaceutical composition is provided comprising the N-2 Form; and at least one pharmaceutically acceptable carrier and/or diluent.

In still another embodiment, a pharmaceutical composition comprises substantially pure Form N-2; and at least one pharmaceutically acceptable carrier and/or diluent.

In still an even further embodiment, a therapeutically effective amount of Form N-2 is combined with at least one pharmaceutically acceptable carrier and/or diluent to provide at least one pharmaceutical composition.

The names used herein to characterize a specific form, e.g. "N-2" etc., should not be considered limiting with respect to any other substance possessing similar or identical physical and chemical characteristics, but rather it should be understood that these designations are mere identifiers that should be interpreted according to the characterization information also presented herein.

BRIEF DESCRIPTION OF THE DRAWINGS

The invention is illustrated by reference to the accompanying drawings described below.

DETAILED DESCRIPTION OF THE INVENTION

Figure 1:
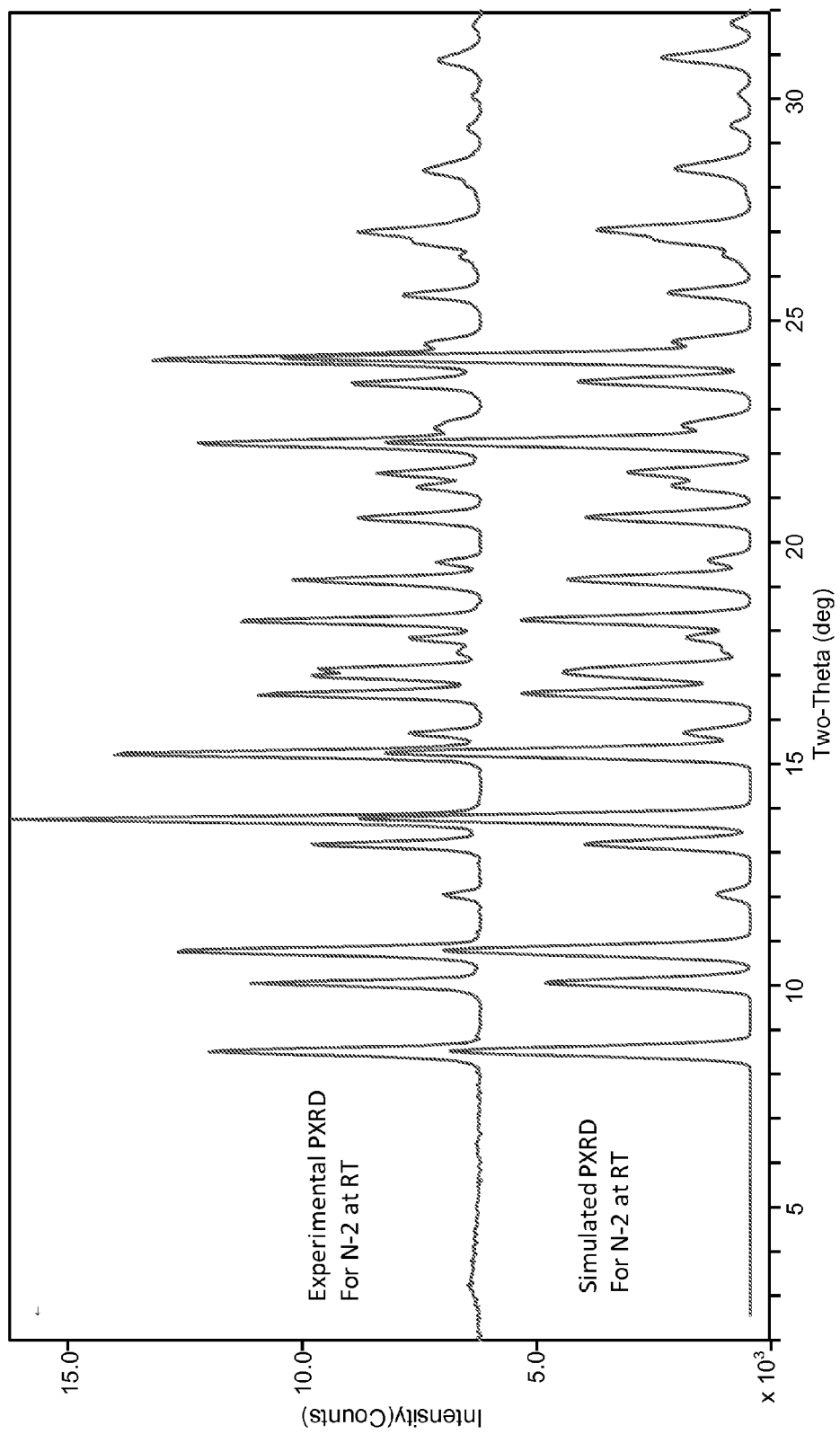
FIG. 1 shows observed and simulated powder x-ray diffraction patterns (CuKα λ=1.5418 Å at T=25° C.) of the N-2 crystalline form of N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide (Compound I).

As used herein, "polymorphs" refer to crystalline forms having the same chemical compositions but different spatial arrangements of the molecules and/or ions forming the crystals.

As used herein, "amorphous" refers to a solid form of a molecule and/or ions that is not crystalline. An amorphous solid does not display a definitive X-ray diffraction pattern with sharp maxima.

As used herein, "substantially pure", when used in reference to a crystalline form, means a sample of the crystalline form of the compound having a purity greater than 90 weight %, including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of Compound I may be deemed substantially pure in that it has a purity greater than 90 weight % of the crystalline form of Compound I, as measured by means that are at this time known and generally accepted in the art, where the remaining less than 10 weight % of material comprises other form(s) of Compound I and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the unit cell parameter "molecules/unit cell" refers to the number of molecules of Compound I in the unit cell.

When dissolved, the crystalline form of Compound I loses its crystalline structure, and is therefore referred to as a solution of Compound I. Crystalline Form N-2 of Compound I may be used for the preparation of liquid formulations in which the compound is dissolved or suspended. In addition, the crystalline Form N-2 of Compound I may be incorporated into solid formulations.

A therapeutically effective amount of the crystalline Form N-2 of Compound I may be combined with a pharmaceutically acceptable carrier or diluent to provide pharmaceutical compositions of this invention. By "therapeutically effective amount", it is meant an amount that, when administered alone or an amount when administered with an additional therapeutic agent, is effective to prevent, suppress, or ameliorate a disease or condition or the progression of a disease or condition.

Compound I, of the formula,

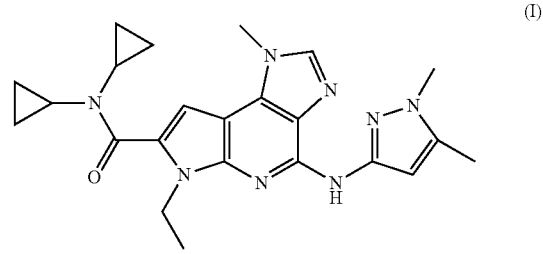 [SMILES: CCn1c(C(=O)N(C2CC2)C2CC2)cc2c3c(ncn3C)c(Nc3cc(C)n(C)n3)nc21]

(I)

is provided as a crystalline material comprising the first crystalline form. The crystalline form of compound I comprises a neat crystalline form referred to herein as "Form N-2" or "N-2 Form".

In one embodiment, the N-2 Form is characterized by unit cell parameters approximately equal to the following:

Cell Dimensions:
a=13.4233 (2) Å
b=10.4312 (2) Å
c=16.3355 (2) Å
α=90.0°
β=90.4750 (10) °
γ=90.0°

Space group: $P2_1/n$

Molecules/asymmetric unit: 1

Number of molecules in the unit cell=4

Volume/Number of molecules in the unit cell=571.81 (6) Å$^3$

Density (calculated)=1.256 Mg/m$^3$, wherein the unit cell parameters of Form N-2 are measured at a temperature of about 23° C.

The crystalline form is a neat crystalline form of Compound I and is referred herein as the "N-2 Form".

In a different embodiment, the N-2 Form of Compound I is characterized by fractional atomic coordinates substantially as listed in Table 1.

TABLE 1

Positional Parameters and Isotropic Temperature Factors for Form N-2 of Compound I

| Atom | X | Y | Z | U(eq) |
|---|---|---|---|---|
| C(1) | 6101(2) | −4208(2) | 4416(2) | 90(1) |
| C(2) | 4413(2) | −3248(2) | 3303(1) | 82(1) |
| C(3) | 4627(1) | −2768(2) | 4147(1) | 56(1) |
| C(4) | 4174(1) | −1826(2) | 4596(1) | 52(1) |
| C(5) | 4702(1) | −1779(2) | 5328(1) | 46(1) |
| C(6) | 3865(1) | −124(2) | 6173(1) | 42(1) |
| C(7) | 3923(1) | 537(2) | 6931(1) | 44(1) |
| C(8) | 3194(1) | 1394(2) | 7157(1) | 44(1) |
| C(9) | 2367(1) | 1615(2) | 6633(1) | 42(1) |
| C(10) | 2409(1) | 895(2) | 5907(1) | 39(1) |
| C(11) | 1463(1) | 2303(2) | 6616(1) | 45(1) |
| C(12) | 974(1) | 1998(2) | 5900(1) | 41(1) |
| C(13) | 4342(1) | 1210(2) | 8109(1) | 61(1) |
| C(14) | 2953(2) | 2760(2) | 8416(1) | 75(1) |
| C(15) | 1405(1) | 608(2) | 4639(1) | 46(1) |
| C(16) | 1918(2) | 1407(2) | 3999(1) | 64(1) |
| C(17) | 14(1) | 2451(2) | 5567(1) | 43(1) |
| C(18) | −746(1) | 2589(2) | 6960(1) | 53(1) |
| C(19) | −1597(2) | 1805(2) | 7273(1) | 73(1) |
| C(20) | −562(2) | 1288(2) | 7286(1) | 65(1) |
| C(21) | −1558(1) | 3510(2) | 5746(1) | 56(1) |
| C(22) | −1408(2) | 4759(2) | 5340(1) | 75(1) |
| C(23) | −1892(2) | 4711(2) | 6153(2) | 79(1) |
| N(1) | 5373(1) | −3230(2) | 4613(1) | 62(1) |
| N(2) | 5434(1) | −2635(2) | 5358(1) | 62(1) |
| N(3) | 4598(1) | −993(1) | 6009(1) | 52(1) |
| N(4) | 4649(1) | 428(2) | 7538(1) | 56(1) |
| N(5) | 3472(1) | 1824(1) | 7919(1) | 54(1) |
| N(6) | 3111(1) | 53(1) | 5655(1) | 41(1) |
| N(7) | 1561(1) | 1137(1) | 5461(1) | 40(1) |
| N(8) | −708(1) | 2846(1) | 6095(1) | 46(1) |
| O(1) | −136(1) | 2496(1) | 4823(1) | 57(1) |

Table 1. Atomic coordinates (×10$^4$) and equivalent isotropic displacement parameters (Å$^2$ × 10$^3$) for N-2.

In a still different embodiment, the N-2 Form of Compound I is characterized by a powder x-ray diffraction pattern substantially in accordance with that shown in FIG. 1.

Figure 2:
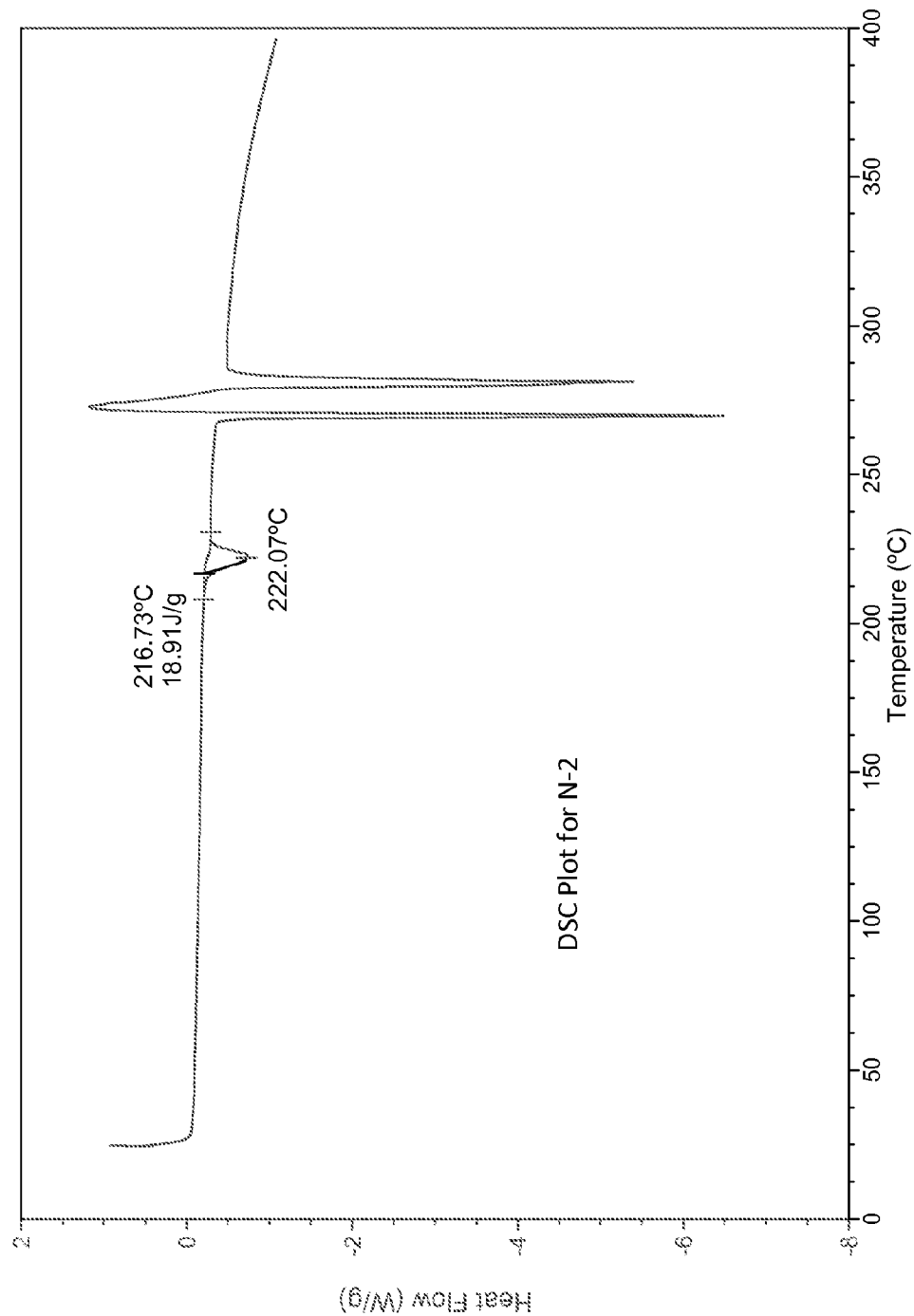
FIG. 2 shows a differential scanning calorimetry thermogram of the N-2 crystalline form of Compound I.

In a further embodiment, the N-2 Form of Compound I is characterized by a differential scanning calorimetry thermogram substantially in accordance with that shown in FIG. 2. The N-2 Form may be characterized by a solid state transition typically at 220±6° C., however, variability is expected due to the kinetic nature of this transition.

In a still further embodiment, the N-2 Form of Compound I is characterized by a powder x-ray diffraction pattern (CuKα λ=1.5418 Å) comprising four or more 2θ values, preferably comprising five or more 2θ values, selected from the group consisting of: 8.5±0.2, 10.0±0.2, 10.8±0.2, 13.2±0.2, 13.7±0.2, 15.2±0.2, 16.6±0.2, 18.2±0.2, 19.1±0.2, 20.5±0.2, 22.2±0.2 and 24.1±0.2, at room temperature.

In another embodiment, the N-2 Form is in substantially pure form. This crystalline form of Compound I in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-2 crystalline form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In one embodiment, the N-2 Form is in substantially pure form, wherein substantially pure is greater than 90 weight % pure, preferably greater than 95 weight % pure, and more preferably greater than 99 weight % pure.

In a different embodiment, a composition is provided consisting essentially of the crystalline Form N-2 of Compound I. The composition of this embodiment may comprise at least 90 weight %, preferably at least 95 weight %, and more preferably at least 99 weight % of the crystalline Form N-2 of Compound I, based on the weight of Compound I in the composition.

Figure 3:
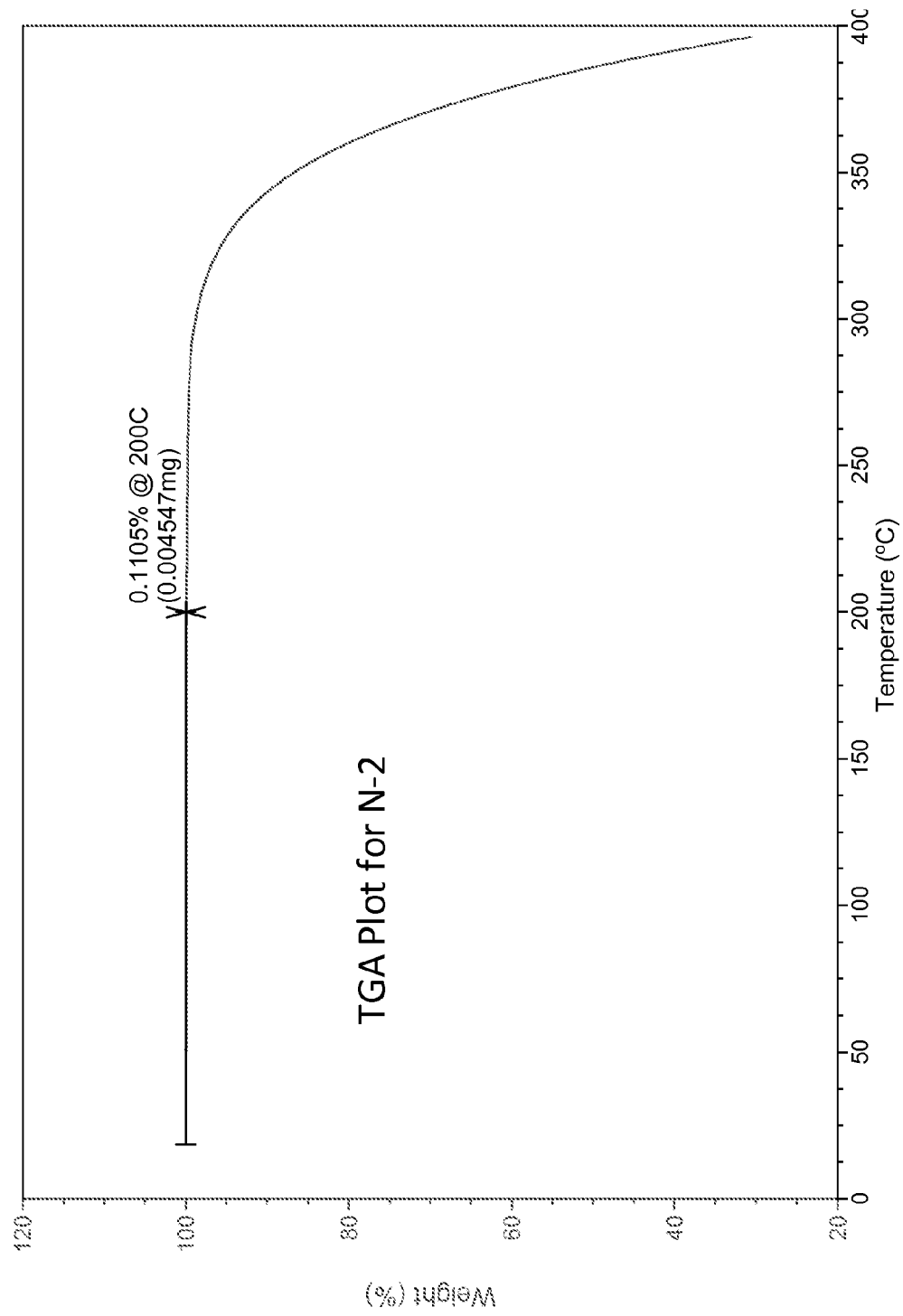
FIG. 3 shows a thermogravimetric analysis (TGA) thermogram of the N-2 crystalline form of Compound I.

In yet another embodiment, the N-2 crystalline form of Compound I may be characterized by a thermogravimetric analysis (TGA) thermogram having minimal weight loss in accordance to a neat form. The invention also provides Form N-2 crystal that exhibits a TGA thermogram substantially the same as shown in FIG. 3.

The present invention also provides a pharmaceutical composition comprising a crystalline form of Compound I, wherein Compound I is in Form N-2; and a pharmaceutically acceptable carrier or diluent. The pharmaceutical composition may comprise the Form N-2 in substantially pure form.

In one embodiment, an oral dosage form is provided comprising Compound I wherein Compound I is in a crystalline form comprising Form N-2. The oral dosage form may comprise Compound I wherein Compound I consists essentially of Form N-2. Alternatively, the oral dosage form may comprise Compound I wherein Compound I is in substantially pure form. A suitable amount of Compound I in the oral dosage form is, for example, in the range of from about 1 to 500 mg.

The present invention further provides a method for treating a proliferative disease, comprising administering to a mammalian species in need thereof, a therapeutically effective amount of Compound I, wherein Compound I is provided in a crystalline form comprising Form N-2. Preferably, Compound I consists essentially of Form N-2. Preferably, the mammalian species is human.

Compound I in Form N-2 may be formulated with a pharmaceutical vehicle or diluent for oral, intravenous, or subcutaneous administration. The pharmaceutical composition can be formulated in a classical manner using solid or liquid vehicles, diluents, and/or additives appropriate to the desired mode of administration. Orally, Form N-2 of Compound I can be administered in the form of tablets, capsules, granules, powders, and the like. Crystalline Form N-2 of Compound I may also be administered as a suspension using carriers appropriate to this mode of administration.

The effective amount of Compound I may be determined by one of ordinary skill in the art, and includes exemplary dosage amounts for a mammal of from about 0.05 to about 300 mg/kg/day, preferably less than about 200 mg/kg/day, in a single dose or in 2 to 4 divided doses. It will be understood that the specific dose level and frequency of dosage for any particular subject may be varied and will depend upon a variety of factors, the bioavailability of Compound I in Form N-2, the metabolic stability and length of action of Compound I, the species, age, body weight, general health, sex, and diet of the subject, the mode and time of administration, rate of excretion, drug combination, and severity of the particular condition. Preferred subjects for treatment include animals, most preferably mammalian species such as humans and domestic animals such as dogs, cats, horses, and the like.

Exemplary compositions for oral administration include suspensions comprising particles of Compound I in Form N-2 dispersed in a liquid medium. The suspension may further comprise, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate, and/or lactose and/or other excipients, binders, extenders, disintegrants, diluents, and lubricants such as those known in the art. Compound I in Form N-2 also may be delivered by sublingual and/or buccal administration, e.g. with molded, compressed, or freeze-dried tablets. Exemplary compositions may include fast-dissolving diluents such as mannitol, lactose, sucrose, and/or cyclodextrins. Also, included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g.,) GANTREZ®); and agents to control release such as polyacrylic copolymer (CARBOPOL 934®). Lubricants, glidants, flavors, coloring agents, and stabilizers may also be added for ease of fabrication and use.

An example of a composition for oral administration is Compound I in crystalline Form N-2, lactose monohydrate (intra-granular phase), microcrystalline cellulose (intra-granular phase), croscarmellose sodium (intra-granular phase), hydroxypropyl cellulose (intra-granular phase), microcrystalline cellulose (extra-granular phase), croscarmellose sodium (extra-granular phase), and magnesium stearate (extragranular phase).

Typically, the solid form of a pharmaceutically active material is important in the preparation of a solid dosage form, such as tablets or capsules as the manufacturing, stability, and/or the performance of the pharmaceutically active material can be dependent upon the solid form. Generally, a crystalline form provides pharmaceutically active material with uniform properties, such as solubility, density, dissolution rate, and stability. In the present invention, Compound I in the crystalline Form N-2 has properties suitable for the manufacture of tablets or capsules, for providing a stable oral dosage form, and/or for delivery of Compound I to a patient in need thereof.

Methods of Preparation and Characterization

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, pp. 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, powder x-ray diffraction, or the like, to assure formation of the preferred crystalline form of the product. The resulting crystalline form may be produced in an amount of greater than about 70 weight % isolated yield, preferably greater than 90 weight % isolated yield, based on the weight of the compound originally employed in the crystallization procedure. The product may be co milled or passed through a mesh screen to delump the product, if necessary.

Crystalline forms may be prepared directly from the reaction medium of the final process for preparing Compound I. This may be achieved, for example, by employing in the final process step a solvent or a mixture of solvents from which Compound I may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one crystalline form and/or polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one crystalline form and/or polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963).

Form N-2 of Compound I according to the invention may be characterized using various techniques, the operation of which are well known to those of ordinary skill in the art. Form N-2 of Compound I may be characterized and distinguished using single crystal x-ray diffraction performed under standardized operating conditions and temperatures, which is based on unit cell measurements of a single crystal of the form at a fixed analytical temperature. The approximate unit cell dimensions in Angstroms (Å), as well as the crystalline cell volume, spatial grouping, molecules per cell, and crystal density may be measured, for example at a sample temperature of 25° C. A detailed description of unit cells is provided in Stout & Jensen, X-Ray Structure Determination: A Practical Guide, Macmillan Co., New York (1968), Chapter 3, which is herein incorporated by reference.

Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (NMR), differential scanning calorimetry, thermography, and gross examination of the crystalline or amorphous morphology. These parameters may also be used in combination to characterize the subject form.

The crystalline form was analyzed using one or more of the testing methods described below.

Single Crystal X-Ray Measurement

Single crystal X-ray data were collected on a Bruker AXS APEX II diffractometer with MicroStarH generator using Cu Kα radiation (λ=1.5418 Å). Indexing and processing of the measured X-ray intensity data were carried out with the APEX2 software suite (Bruker AXS, Inc., Madison, Wis., USA). The structure was solved by direct methods and refined on the basis of observed reflections using SHELXTL crystallographic package (Bruker AXS, Inc., Madison, Wis., USA). The derived atomic parameters (coordinates and temperature factors) were refined through full matrix least-squares. The function minimized in the refinements was $\Sigma_w(|F_O|-|F_C|)^2$. R is defined as $\Sigma||F_O|-|F_C||/\Sigma|F_O|$, while $R_w=[\Sigma_w(|F_O|-|F_C|)^2/\Sigma_w|F_O|^2]^{1/2}$, where w is an appropriate weighting function based on errors in the observed intensities. All non-hydrogen atoms were refined with anisotropic thermal displacement parameters. Hydrogen atoms were calculated from an idealized geometry with standard bond lengths and angles and refined using a riding model.

DSC (Open Pan)

DSC experiments were performed in a TA INSTRUMENTS® model Q2000 or Q1000. The sample (about 2-10 mg) was weighed into an aluminum pan and the weight recorded accurately to a hundredth of a milligram, and transferred to the DSC. The instrument was purged with nitrogen gas at 50 mL/min. Data were collected between room temperature and 300° C. at a heating rate of 10° C./min. The plot was made such that endothermic peaks point down.

TGA (Open Pan)

TGA experiments were performed in a TA INSTRUMENTS® model Q5000 or Q500. The sample (about 4-30 mg) was placed in a previously tared platinum pan. The weight of the sample was measured accurately and recorded to a thousandth of a milligram by the instrument. The furnace was purged with nitrogen gas at 100 mL/min. Data were collected between room temperature and 300° C. at a heating rate of 10° C./min.

PXRD

PXRD data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected approximately for 2≤2θ≤35° with a sample exposure time of at least 1000 seconds. The resulting two-dimensional diffraction arcs were integrated to create a traditional 1-dimensional PXRD pattern with a step size of 0.05 degrees 2θ in the approximate range of 2 to 32 degrees 2θ.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth below, but rather is defined by the claims appended hereto.

Example 1

Preparation of Form N-2 of Compound I

Crystal form N-2 (neat form) was prepared by dissolving 5 mg of Compound I in a mixture of acetonitrile (0.4 mL) and dichloromethane (0.1 mL) by heating a solution up to 60° C. Yellow plate-shaped crystals of N-2 were obtained after one day of slow evaporation of solution at room temperature.

Example 2

Preparation of Form N-2 of Compound I 25.5 L of rich organic (containing 1000 grams of Compound I in solution) was polish filtered into a crystallizer with jacket set to 25° C., followed by 1.0 L of methylene chloride to rinse the polish filter. The jacket was then set to 50° C., and the reaction stream was distilled at atmospheric pressure to 5.00 L, with a control point in place to ensure water content less than 500 ppm prior to seeding. Jacket was then cooled to 35° C., and a vessel rinse of 1.50 L methylene chloride was added to dissolve any solid precipitate from the crystallizer walls. After visual confirmation that the solution was clear at 6.50 L, the batch was cooled to 15° C. and then seeded with 0.035 kg jet milled Compound I. The batch was cooled to 10° C. over 30 minutes, and then 6.50 L of acetone was charged over 60 minutes. The vessel was depressurized to 200 mbar, jacket temperature set to 45° C., and the batch was distilled to 8.00 L. Vacuum distillation continued at 200 mbar, and an additional 8.00 L of acetone was charged during distillation to maintain constant batch volume of 8.00 L. Following distillation endpoint, the jacket temperature was cooled while maintaining the batch under internal reflux. Once both the jacket and batch temperature had cooled below 15° C., the batch was re-pressurized to atmospheric pressure. The batch was then cooled to 5° C., aged for 60 min, discharged and isolated on a filter. The cake was washed with 3.0 L of cold (5° C.) acetone, then reslurried twice in 3.0 L of cold (5° C.) acetone. The cake was dried at 50° C. under full vacuum until constant weight obtained. The recovered yield was 967 grams of Compound I (93.4 mol %).

Example 3

Preparation of Tablets Comprising Form N-2 of Compound I

Two clinical capsule formulations were developed using dry granulation. The composition is shown below:
40 mg strength (15% drug load)

| Ingredients | % w/w | mg |
|---|---|---|
| Compound I (Form N-2) | 15.0 | 40 |
| Microcrystalline Cellulose, | 40.75 | 108.67 |
| Lactose, Anhydrous | 40.75 | 108.67 |
| Croscarmellose Sodium | 3 | 8 |
| Magnesium Stearate | 0.5 | 1.33 |
| Total: | 100 | 266.67 |

5 mg strength (2.5% drug load)

| Ingredients | % w/w | mg |
|---|---|---|
| Compound I (Form N-2) | 2.5 | 5 |
| Microcrystalline Cellulose, PH 102 | 47 | 94 |
| Lactose, anhydrous DC | 47 | 94 |
| Croscarmellose Sodium | 3 | 6 |
| Magnesium Stearate | 0.5 | 1 |
| Total: | 100 | 200.0 |

As previously noted, the N-2 form was selected due to a number of properties including chemical/physical stability, reproducibility and hygroscopicity. With regard to stability, it was found that this form is stable under accelerated conditions of temperature and humidity for up to 4 weeks and on exposure to UV/HIL for 4 days. Additionally, it was found that milled Form N-2 API is also stable up to 2 weeks under high humidity and temperature open dish conditions (25° C./60% RH and 40° C./75% RH open).

What is claimed is:

1. A crystalline form of Compound I:

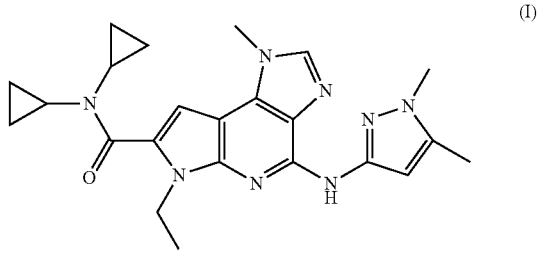 [SMILES: CCn1c(C(=O)N(C2CC2)C2CC2)cc2c3c(ncn3C)c(Nc3cc(C)n(C)n3)nc21]

(I)

characterized by one or more of the following:
Cell dimensions: a=13.4233(2) Å
b=10.4312(2) Å
c=16.3355(2) Å
$\alpha$=90°
$\beta$=90.4750(10)°
$\gamma$=90°
Space group: $P2_1/n$
Molecules/asymmetric unit: 1
wherein measurement of said crystalline form is at a temperature of about 23° C.; and/or
b) a powder x-ray diffraction pattern comprising five or more 2θ values (CuKα λ=1.5418 Å) selected from the group consisting of 8.5±0.2, 10.0±0.2, 10.8±0.2, 13.2±0.2, 13.7±0.2, 15.2±0.2, 16.6±0.2, 18.2±0.2, 19.1±0.2, 20.5±0.2, 22.2±0.2 and 24.1±0.2, wherein measurement of said crystalline form is at room temperature.

2. A pharmaceutical composition comprising the crystalline form according to claim 1 and a pharmaceutically acceptable carrier or diluent.

\* \* \* \* \*